United States Patent [19]  [11] 4,294,772
Martin  [45] Oct. 13, 1981

[54] OXIME DERIVATIVES FOR PROTECTING PLANT CROPS

[75] Inventor: Henry Martin, Allschwil, Switzerland

[73] Assignee: Ciba-Geigy Corporation, Ardsley, N.Y.

[21] Appl. No.: 68,262

[22] Filed: Aug. 20, 1979

[30] Foreign Application Priority Data

Aug. 31, 1978 [CH] Switzerland ............ 9200/78

[51] Int. Cl.³ .................................... C07F 7/22
[52] U.S. Cl. .................... 260/429.7; 546/192; 546/300; 71/88; 546/330; 548/100; 71/90; 548/101; 548/179; 71/92; 548/198; 548/238; 71/93; 548/255; 549/3; 71/94; 549/77; 71/95; 71/97; 71/100; 71/106; 71/108; 71/109; 71/111; 71/115; 71/118; 71/120; 260/326.62; 260/326.8; 260/340.5 R; 260/340.6; 260/345.1; 260/345.2; 260/346.22; 260/347.7; 260/348.39; 544/59; 544/163; 544/225; 544/335; 544/356; 546/174; 546/184
[58] Field of Search ............ 260/429.7; 71/97, 105; 424/288

[56] References Cited

U.S. PATENT DOCUMENTS

| 3,131,509 | 5/1964 | Hoffmann | 71/77 |
| 3,234,255 | 2/1966 | Hackmann et al. | 71/121 |
| 3,275,659 | 9/1966 | Weissenberger | 71/97 |
| 3,282,672 | 11/1966 | Weissenberger | 71/97 |
| 3,419,662 | 12/1968 | Weissenberger | 424/288 |
| 4,020,106 | 4/1977 | Ackerley et al. | 260/429.7 |
| 4,158,001 | 6/1979 | Reuther et al. | 260/429.7 |

Primary Examiner—Glennon H. Hollrah
Attorney, Agent, or Firm—Frederick H. Rabin

[57] ABSTRACT

Tin-containing oxime derivatives of the formula

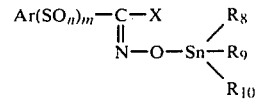

wherein
n is 0, 1 or 2,
m is 0 or 1,
Ar is an optionally substituted phenyl radical or an optionally substituted naphthyl radical, or when m is 0, Ar may also be an ester group,
X is hydrogen, —CN, halogen, lower alkyl, lower alkanoyl, —COOH, a carboxylic acid ester radical, a carbamoyl radical and
$R_8$, $R_9$ and $R_{10}$, each independently of the other, are alkyl, aryl, aralkyl or $C_3$-$C_7$ cycloalkyl, are suitable for protecting cultivated plants from the phytotoxic action of aggressive agrochemicals, in particular herbicides preferred are compounds of the above formula in which
Ar is alkylphenyl, alkoxyphenyl, halophenyl, naphthyl or amido,
X is cyano or a carboxylic acid ester radical, and
$R_8$, $R_9$ and $R_{10}$ are the same and are $C_1$-$C_4$ alkyl, benzyl or phenyl.

5 Claims, No Drawings

OXIME DERIVATIVES FOR PROTECTING PLANT CROPS

The present invention relates to compositions for protecting crops of cultivated plants which contain, as active component, an oxime derivative of the formula I

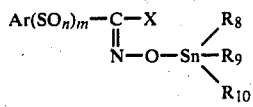

wherein n is 0, 1 or 2 and m is 0 or 1, and
Ar is a phenyl radical

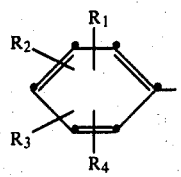

a naphthyl radical substituted by $R_2$ and $R_3$, a 5- to 10-membered heterocyclic radical which contains not more than 3 identical or different heteroatoms N, O and/or S and which is substituted by $R_2$, $R_3$ and $R_4$ and can be substituted by oxo or thiono, or if m is 0, Ar is a radical R-CO, wherein R is a radical $-OR_5$, in which $R_5$ is an aliphatic group containing not more than 8 carbon atoms or is an araliphatic group containing not more than 15 carbon atoms or is a cycloaliphatic or aromatic group, each containing not more than 10 carbon atoms, while the possible substituents of the aromatic radicals or of the cycloaliphatic radical are halogen, —CN, —NO$_2$, lower alkyl, lower alkoxy, haloalkyl; or R is a radical $-NH-CO-NH-R_7$ or a radical $-N(R_6)(R_7)$, wherein $R_6$ is hydrogen or lower alkyl and $R_7$ is hydrogen or an aliphatic group containing not more than 8 carbon atoms or an araliphatic group containing not more than 15 carbon atoms, or a cycloaliphatic or aromatic group each containing not more than 10 carbon atoms, while possible substituents of the aromatic groups or of the cycloaliphatic radical are halogen, —CN, NO$_2$, lower alkyl, lower alkoxy, or haloalkyl; or R is a radical $-N(R_6)(R_7)$, wherein $R_6$ and $R_7$ together form a 5- or 6-membered heterocyclic ring which can additionally contain oxygen as possible further heteroatom, $R_1$ is hydrogen, halogen, lower alkyl, lower alkoxy or a p-phenoxy radical which is unsubstituted or at most disubstituted by halogen, CN, NO$_2$, CF$_3$, $R_2$, $R_3$ and $R_4$, each independently of the other, are hydrogen, halogen, CN, NO$_2$, lower alkyl, lower alkoxy, haloalkyl, haloalkoxy, lower alkanoyl, OH, phenyl, halophenyl, lower carbalkoxy, lower alkoxycarbonyl, lower alkoxycarbonyloxy, lower carbamoyloxy, lower alkylthio, lower alkylsulfonyl, phenalkoxy, cyclohexyl, NH$_2$, —NH-lower alkyl, —N(di-lower alkyl), lower alkanoylamino, carbamoyl, sulfamoyl, X is hydrogen, —CN, halogen, lower alkyl, lower alkanoyl, —COOH, a carboxylic acid ester radical, a carbamoyl radical, and $R_8$, $R_9$ and $R_{10}$, each independently of the other, are alkyl, aryl, aralkyl or $C_3$-$C_7$ cycloalkyl.

Carboxylic acid esters are lower alkyl esters. Carbamoyl radicals, in addition to —CONH$_2$, are also monoalkyl- substituted or symmetrically or unsymmetrically dialkyl-substituted amides, in which the alkyl groups are lower alkyl groups.

The term alkyl by itself or as moiety of another substituent comprises branched or unbranched alkyl groups of 1 to 8 carbon atoms. Lower alkyl by itself or as moiety of another substituent denotes $C_1$-$C_4$alkyl. Examples are methyl, ethyl, propyl, isopropyl, butyl, isobutyl, sec-butyl, tert-butyl, as well as the higher homologues amyl, isoamyl, hexyl, heptyl, octyl, together with their isomers. By analogy, alkanoyl groups contain an additional carbon atom.

$C_3$-$C_7$Cycloalkyl groups are cyclopropyl, cyclobutyl, cyclopentyl, cyclohexyl and cycloheptyl groups. Aryl denotes in particular unsubstituted or substituted phenyl and naphthyl. Cyaloaliphatic radicals comprise both cycloalkyl and cycloalkenyl radicals.

The following mono- and bicyclic radicals are examples of suitable 5- to 10-membered heterocyclic radicals: furan, nitrofuran, bromofuran, methylfuran, thiophene, chlorothiophene, pyridine, 2,6-dichloropyridine, pyrimidine, pyridazine, pyrazine, piperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane, 1,4-oxathi-(2)-ine, benzofurane, benzpyrazole, benzoxazole, quinoline.

The compounds of the formula I can be obtained by reacting a compound of the formula II

with the desired tin halide of the formula III

In the above formulae (II) and (III), the symbols Ar, $R_8$, $R_9$, $R_{10}$, X, m and n are as defined for formula (I), Me is hydrogen or a cation, preferably the cation of an alkali metal or alkaline earth metal, and Hal is halogen, preferably chlorine or bromine. (Cf. Organic Reactions 1953, Vol. 7, page 343 and 373; Journal d. prakt. Chemie 66, page 353; Liebigs Ann. 250, 165).

Suitable solvents employed in the reaction for obtaining the compounds of the formula (I) are in principle all those which are inert under the reaction conditions, e.g. hydrocarbons, but in particular polar solvents such as acetonitrile, dioxane, cellosolve, dimethyl formamide, and also ketones, such as methyl ethyl ketone and acetone. Solvents which contain hydroxyl groups are excluded.

The reaction temperatures are in the range from $-10°$ C. to about $+150°$ C., preferably from 20° to 120° C.

Where Me is hydrogen in formula (II), the process is carried out in the presence of a base. Examples of suitable bases are inorganic bases, such as the oxides, hydroxides, hydrides, carbonates and bicarbonates of alkali metals and alkaline earth metals, as well as e.g. tertiary amines, such as triethylamine, triethylenediamine, piperidine and pyridine. The process also constitutes an object of the invention.

The compounds of the formula I can be used by themselves or together with suitable carriers and/or other adjuvants. Suitable carriers and adjuvants can be solid or liquid and correspond to the substances normally used in the art of formulation, for example natural or regenerated mineral substances, solvents, dispersants, wetting agents, tackifiers, thickeners, binders or fertilisers.

The content of active substance in commerical compositions is between 0.1% and 90% by weight.

For application, the compounds of the formula I may be processed to the following formulations (in which the percentages by weight in brackets refer to advantageous amounts of active ingredient):

Solid formulations:
dusts, tracking agents, (up to 10%) granules (coated granules, impregnated granules and homogeneous granules); pellets (1 to 80%);

Liquid formulations:
(a) active substance concentrates which are dispersible in water: wettable powders, pastes; (25–90% in commercial packs, 0.01 to 15% in ready for use solutions); emulsifiable concentrates and concentrated solutions (10 to 50%; 0.01 to 15% in ready for use solutions).
(b) Solutions (0.1 to 20%); aerosols.

Such compositions likewise constitute an object of the invention.

Oximes of the formula (I) are exceptionally suitable for protecting crop plants, such as rice, maize, cereals (millet, wheat, rye, barley, oats) from attack by aggressive agrochemicals, in particular herbicides of a very wide variety of compound classes, where the action of these chemicals is not selective or not sufficiently selective, i.e. in addition to the weeds which it is desired to control, the cultivated plants themselves are also damaged to a greater or lesser degree.

Different compounds which are able to antagonise the harmful action of a herbicide on cultivated plants specifically have already been proposed as antidotes, i.e. compounds which protect cultivated plants without noticeably influencing the herbicidal action on the weeds which it is desired to control. Depending on their properties, such antidotes, also known as safeners, can be used for pretreating the seeds of the cultivated plants (dressing seeds or seedlings) or before sowing seeds in furrows or as tank mixture, by themselves or together with the herbicide or after emergence of the plants. The pre-emergence treatment includes both treatment of the crop area before sowing (ppi=pre-plant incorporation) and treatment of the crop areas after sowing but before emergence of the plants.

Thus, British patent specification No. 1 277 557 discloses the treatment of seed and seedlings of wheat and sorghum with certain esters and amides of oxamic acid before attack by N-methoxymethyl-2'-6'-diethylchloroacetanilide (Alachlor). Other publications (German Offenlegungsschriften Nos. 1 952 910 and 2 245 471, and French patent specification No. 2 021 611), propose antidotes for the treatment of cereals, maize seeds and rice seeds to protect them against attack by herbicidal thiolcarbamates. In German patent specification No. 1 576 676 and U.S. Pat. No. 3,131,509, hydroxyamino-acetanilides and hydantoins are suggested for protecting cereal seeds against carbamates, such as IPC, CIPC, etc.

Further developments, however, have shown all these preparations to be unsatisfactory.

Surprisingly, oximes of the formula I have the property of protecting cultivated plants from attack by aggressive agricultural chemicals, in particular herbicides, of the most diverse compound classes, including 1,3,5-triazines, 1,2,4-triazinones, phenylurea derivatives, carbamates, thiolcarbamates, phenoxyacetates, phenoxypropionates, haloacetanilides, halophenoxyacetates, substituted phenoxyphenoxyphenoxyacetates and -propionates, benzoic acid derivatives, where these compounds are not tolerated or insufficiently tolerated by plants.

The rates of application of the antidote with respect to the herbicide depend largely on the mode of application. Where a field treatment is carried out, the ratio of antidote of the formula I to phytotoxic chemical is 1:100 to 5:1, preferably 1:20 to 1:1. When dressing seeds and taking similar specific protective measures, however, much lower amounts of antidote are required in comparison with e.g. the amounts of herbicide later employed per hectare of crop area (e.g. about 1:3000 to 1:1000). As a rule, protective measures such as seed dressing with an antidote of the formula I and possible later field treatment with agrochemicals are only loosely connected. Pretreated seeds and plants can later come into contact with different chemicals in agriculture, horticulture and forestry.

Accordingly, the invention relates to plant protective compositions which contain the oxime ethers of the formula I together with herbicides, and also to compositions which contain the oxime ethers of the formula I as sole active component. Plant protective compositions which contain an antidote (also known as safener) of the formula I can be formulated, marketed or used without the simultaneous presence of the herbicide, the aggressive action of which it is desired to counter. An important utility is seed dressing, which is effected at a time that is entirely independent of the application of the agrochemical, e.g. the herbicide. Another field of use is the treatment of soil still containing residues of a herbicide applied during the previous season and which could damage the new crop of cultivated plants.

The antidote property is one that is independent of the crop plant and of the agricultural chemical, the action of which it is desired to counter selectively. This property is inherent in a composition of the formula I, but it only becomes apparent on the combined action of the three components: antidote- agrochemical-plant. Similar to a pesticidal chemical, the pesticidal action of which only becomes evident in the presence of a pest, evidence of the safener activity also requires the presence of the other two components which participate in the action, namely the agrochemical (e.g. herbicide) and the crop plant. This feature distinguishes a formulated safener composition from a synergistic two- or three-component mixture in which all the active components are simultaneously present and all produce the same effect.

Cultivated plants within the scope of this invention are all plants which, in any form, can be harvested (seeds, roots, stalks, tubers, leaves, blossoms) and from which extracts can be obtained (oils, sugar, starch, protein) and which for this purpose are cultivated and tended. To these plants belong e.g. all species of cereals, maize, rice, millet, soybeans, beans, peas, potatoes, vegetables, cotton, sugar beet, sugar cane, ground nuts, tobacco, hops, and also ornamentals, fruit trees and bananas, cocoa and natural rubber plants. This list does not constitute any limitation.

In principle, an antidote can be employed wherever it is desired to protect a cultivated plant from the phytotoxicity of a chemical.

The invention also relates to a method of protecting cultivated plants from aggressive (phytotoxic) chemicals, which comprises applying an oxime derivative of the formula I which acts as antidote, optionally before or after application of the agrochemical, or also simultaneously with the agrochemical.

The invention also relates to the propagation products of such cultivated plants which are given a protective treatment with an oxime derivative of the formula I. By propagation products are meant all generative parts of plants which can be used for the propagation of the cultivated plant, for example grains (seeds in the narrow sense), roots, fruit, tubers, rhizomes, parts of stalks, branches (seedlings) and other parts of plants. Propagation products also include pregerminated plants and young plants which, after pregermination or emergence, will be further transplanted. Such young plants can be selectively protected by means of a complete or partial immersion treatment before transplantation.

The compounds of the formula I are mentioned in very general form in U.S. Pat. Nos. 3,419,662, 3,275,659 and 3,282,672, and in Japanese published patent specifications 67/24573 and 67/26296, but no reference is made to their action as antidotes. The compounds of the formula I preferred as antidotes are not specifically described in the prior art and are therefore novel.

The novel compounds of the formula I likewise constitute an object of the invention.

On account of their activity, the following types of substituent and combinations thereof are preferred:

1. Ar=

(a)

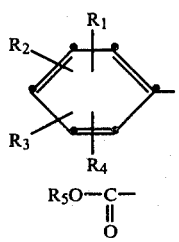

$R_5O-C-$
$\phantom{R_5O-}\|$
$\phantom{R_5O-C}O$ (b)

(c) 1-naphthyl
(d) benzoxazole
(e) benzthiazole

2. X=
   (a) CN
   (b) hydrogen
   (c) lower alkyl
   (d) carboxylic acid ester radical 3.
   (a) m=0
   (b) n=2, m=1

4.
   (a) $R_8=R_9=R_{10}$

Examples of particularly interesting combinations are:

(i) Ar=

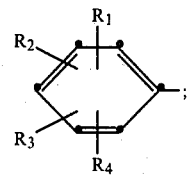

m=0 and X=CN (ii) Ar=

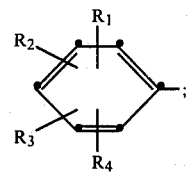

n=2; m=1 and X=CN (iii) Ar=1-naphthyl; m=0 and X=CN (iv) Ar=

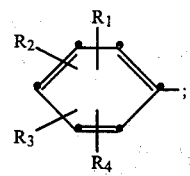

m=0 and X=hydrogen (v) Ar=

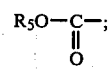

$R_5O-C-$
$\phantom{R_5O-}\|$
$\phantom{R_5O-C}O$ m=0 and X=carboxylic acid ester radical (vi) Ar=benzoxazole and m=0

(vii) Ar=benzthiazole and m=0

(viii) Ar=

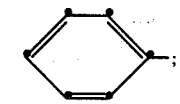

m=0 and X=lower alkyl.

In the above groups, the substituents not mentioned are as defined for formula (I). Preferred compounds within the above groups are those wherein $R_8$, $R_9$ and $R_{10}$ are the same.

Resulting therefrom, accordingly, are e.g. the following preferred groups of compounds:

(a) compounds wherein X is cyano or a carboxylic acid ester radical, Ar is alkylphenyl, alkoxyphenyl, halophenyl, naphthyl or amido, and $R_8$, $R_9$ and $R_{10}$ are the same and are $C_1$-$C_4$alkyl, benzyl or phenyl;

(b) compounds wherein X is cyano, Ar is alkylphenyl, alkoxyphenyl, halophenyl or amido, and $R_8$, $R_9$ and $R_{10}$ are the same and are n-butyl or phenyl.

Particularly interesting individual compounds are:

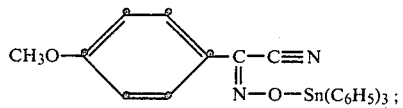

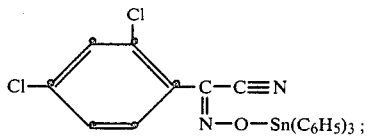

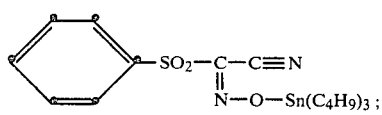

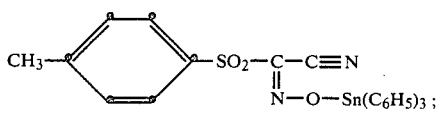

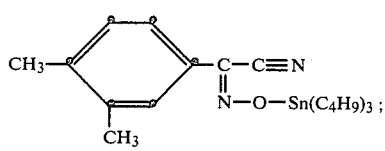

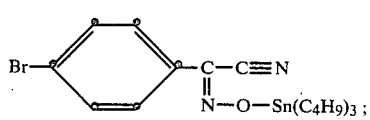

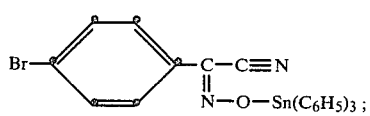

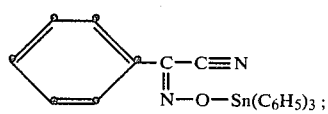

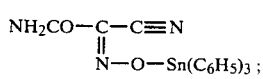

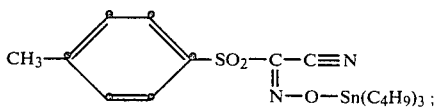

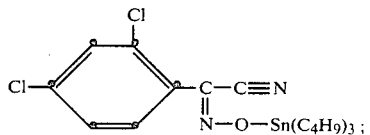

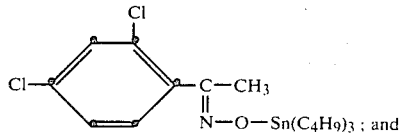

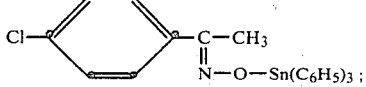

The preferred groups of compounds and individual compounds, compositions containing them and their use in protecting cultivated plants from aggressive agrochemicals also constitute an object of the invention.

The invention is illustrated by the following Examples, but without any restriction to what is described therein. Temperatures are in degrees centigrade, pressures in millibars, and parts and percentages are by weight.

EXAMPLE 1

Manufacture of

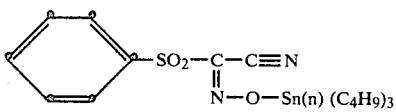

11.6 g (0.05 mole) of the sodium salt of α-phenylsulfonyloximinoacetonitrile and 16.3 g (0.05 mole) of tri-n-butyl tin chloride are dissolved in 50 ml of acetonitrile and the solution is stirred for 2 hours at 40°–50° C. The solution is then concentrated in vacuo at about 50° C. and the residue is stirred in water and methylene chloride until the formation of two phases which separate. The methylene chloride phase is separated, dried over sodium sulfate and concentrated. The final product is obtained in the form of a brown oil; $n_{22}^D = 1.5395$.

EXAMPLE 2

Manufacture of

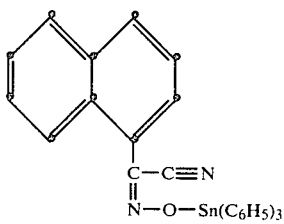

5.5 g (0.025 mole) of the sodium salt of α-naphth-1-yloximinoacetonitrile and 9.6 g (0.025 mole) of triphenyl tin chloride are dissolved in 50 ml of acetonitrile and the solution is refluxed for 4 hours. The fine suspension is then concentrated, the residue is taken up in methylene chloride and the salt is collected by filtration. The filtrate is concentrated, affording the final product with a melting point of 176°–179° C.

EXAMPLE 3

Manufacture of

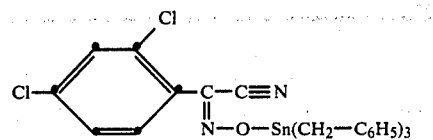

7.1 g (0.03 mole) of the sodium salt of 2,4-dichlorophenyloximinoacetonitrile and 14.2 g of tribenzyl tin chloride are dissolved in 50 ml of acetonitrile and the solution is refluxed for 4 hours. The fine suspension is then concentrated, the residue is taken up in methylene chloride and the salt is collected by filtration. The filtrate is concentrated, affording the final product in the form of an oil which crystallises after standing for some time. Melting point: 89°–93° C.

The following compounds of the formula (I) can be obtained in analogous manner:

TABLE I ($R_1$ = phenyl ring with $R_1$, $R_2$, $R_3$ substituents)

| Compound | $R_1$ | $R_2$ | $R_3$ | X | n | m | $R_8$ | $R_9$ | $R_{10}$ | Physical data (°C.) |
|---|---|---|---|---|---|---|---|---|---|---|
| 1 | H | H | H | CN | — | 0 | $C_4H_9(n)$ | $C_4H_9(n)$ | $C_4H_9(n)$ | $n_{22}^D$ 1.5432 |
| 2 | H | H | H | CN | — | 0 | $C_6H_5$ | $C_6H_5$ | $C_6H_5$ | m.p. 136–139° |
| 3 | H | H | H | CN | — | 0 | $CH_2C_6H_5$ | $CH_2C_6H_5$ | $CH_2C_6H_5$ | m.p. 77–81° |
| 4 | 4-Cl | H | H | CN | — | 0 | $CH_2C_6H_5$ | $CH_2C_6H_5$ | $CH_2C_6H_5$ | m.p. 120–125° |
| 5 | 4-t-$C_4H_9$ | H | H | CN | — | 0 | $C_4H_9(n)$ | $C_4H_9(n)$ | $C_4H_9(n)$ | $n_{22}^D$ 1.5347 |
| 6 | 4-$CH_3$ | H | H | CN | — | 0 | $C_4H_9(n)$ | $C_4H_9(n)$ | $C_4H_9(n)$ | $n_{22}^D$ 1.5417 |
| 7 | 4-$CH_3$ | H | H | CN | — | 0 | $C_6H_5$ | $C_6H_5$ | $C_6H_5$ | m.p. 127–131° |
| 8 | 4-$OCH_3$ | H | H | CN | — | 0 | $C_4H_9(n)$ | $C_4H_9(n)$ | $C_4H_9(n)$ | $n_{22}^D$ 1.5483 |
| 9 | 4-$OCH_3$ | H | H | CN | — | 0 | $C_6H_5$ | $C_6H_5$ | $C_6H_5$ | resin |
| 10 | 4-$OCH_3$ | H | H | CN | — | 0 | $CH_2C_6H_5$ | $CH_2C_6H_5$ | $CH_2C_6H_5$ | m.p. 89–93° |
| 11 | 2-Cl | 4-Cl | H | CN | — | 0 | $CH_2C_6H_5$ | $CH_2C_6H_5$ | $CH_2C_6H_5$ | |
| 12 | 3-Cl | 4-Cl | H | CN | — | 0 | $CH_2C_6H_5$ | $CH_2C_6H_5$ | $CH_2C_6H_5$ | m.p. 90–95° |
| 13 | 4-Br | H | H | CN | — | 0 | $C_4H_9(n)$ | $C_4H_9(n)$ | $C_4H_9(n)$ | resin |
| 14 | 4-Br | H | H | CN | — | 0 | $C_6H_5$ | $C_6H_5$ | $C_6H_5$ | m.p. 134–138° |
| 15 | 4-Cl | H | H | CN | — | 0 | $C_6H_5$ | $C_6H_5$ | $C_6H_5$ | m.p. 135–139° |
| 16 | 4-Cl | H | H | CN | — | 0 | $C_4H_9(n)$ | $C_4H_9(n)$ | $C_4H_9(n)$ | oil |
| 17 | 2-Cl | 4-Cl | H | CN | — | 0 | $C_4H_9(n)$ | $C_4H_9(n)$ | $C_4H_9(n)$ | wax-like |
| 18 | 2-Cl | 4-Cl | H | CN | — | 0 | $C_6H_5$ | $C_6H_5$ | $C_6H_5$ | m.p. 138–139° |
| 19 | H | H | H | $COOC_2H_5$ | — | 0 | $C_4H_9(n)$ | $C_4H_9(n)$ | $C_4H_9(n)$ | m.p. 48–53° |
| 20 | 4-Br | H | H | CN | — | 0 | pyridyl-H | pyridyl-H | pyridyl-H | |
| 21 | 4-Cl | H | H | CN | — | 0 | $CH_3$ | $C_4H_9(n)$ | $C_4H_9(n)$ | |
| 22 | H | H | H | Cl | — | 0 | $C_4H_9(n)$ | $C_4H_9(n)$ | $C_4H_9(n)$ | |
| 23 | H | H | H | C(=O)—$CH_3$ | — | 0 | $C_6H_5$ | $C_6H_5$ | $C_4H_9(n)$ | |
| 24 | H | H | H | H | — | 0 | $C_4H_9(n)$ | $C_4H_9(n)$ | $C_4H_9(n)$ | |
| 25 | 2-Cl | 4-Cl | H | $CH_3$ | — | 0 | $C_4H_9(n)$ | $C_4H_9(n)$ | $C_4H_9(n)$ | |
| 26 | H | H | H | C(=O)NH$CH_3$ | — | 0 | $C_4H_9(n)$ | $C_4H_9(n)$ | $C_4H_9(n)$ | |
| 27 | 3-$CF_3$ | H | H | CN | — | 0 | $C_4H_9(n)$ | $C_4H_9(n)$ | $C_4H_9(n)$ | $n_{16}^D$ 1.5132 |
| 28 | H | H | H | CN | 2 | 1 | $C_4H_9(n)$ | $C_4H_9(n)$ | $C_4H_9(n)$ | $n_{22}^D$ 1.5995 |
| 29 | H | H | H | CN | 2 | 1 | $C_6H_5$ | $C_6H_5$ | $C_6H_5$ | m.p. 147–150° |
| 30 | 4-$CH_3$ | H | H | CN | 2 | 1 | $C_4H_9(n)$ | $C_4H_9(n)$ | $C_4H_9(n)$ | $n_{22}^D$ 1.5392 |
| 31 | 4-$CH_3$ | H | H | CN | 2 | 1 | $C_6H_5$ | $C_6H_5$ | $C_6H_5$ | resin |
| 32 | 4-$NO_2$ | H | H | CN | — | 0 | $C_6H_5$ | $C_6H_5$ | $C_6H_5$ | |
| 33 | 2-F | H | H | CN | — | 0 | $C_6H_5$ | $C_6H_5$ | $C_6H_5$ | |
| 34 | furyl-O | H | H | CN | — | 1 | $C_4H_9(n)$ | $C_4H_9(n)$ | $C_4H_9(n)$ | |
| 35 | H | H | H | CN | 0 | 1 | $C_4H_9(n)$ | $C_4H_9(n)$ | $C_4H_9(n)$ | |
| 36 | 3-$CH_3$ | 4-$CH_3$ | H | CN | — | 0 | $C_4H_9(n)$ | $C_4H_9(n)$ | $C_4H_9(n)$ | oil |
| 37 | H | H | H | $COOC_2H_5$ | — | 0 | $C_6H_5$ | $C_6H_5$ | $C_6H_5$ | |
| 38 | 4-Cl | H | H | CN | 2 | 1 | $C_4H_9(n)$ | $C_4H_9(n)$ | $C_4H_9(n)$ | $n_{20}^D$ 1.5470 |
| 39 | H | H | H | $C_2H_5$ | — | 0 | $C_2H_5$ | $C_2H_5$ | $C_4H_9(n)$ | |
| 40 | H | H | H | Cl | — | 0 | $C_6H_5$ | $C_6H_5$ | $C_6H_5$ | |
| 41 | 2-O$CH_3$ (C=O) | H | H | H | — | 0 | $C_4H_9(n)$ | $C_4H_9(n)$ | $C_4H_9(n)$ | |
| 42 | 2-OCNH$CH_3$ (C=O) | H | H | H | — | 0 | $C_6H_5$ | $C_6H_5$ | $C_6H_5$ | |
| 43 | 4-furyl | H | H | $CH_3$ | — | 0 | $CH_2—C_6H_5$ | $CH_2—C_6H_5$ | $CH_2—C_6H_5$ | |
| 44 | 4-CN | H | H | CN | — | 0 | $C_4H_9(n)$ | $C_4H_9(n)$ | $C_4H_9(n)$ | |
| 45 | 2-CN | H | H | CN | — | 0 | $C_4H_9(n)$ | $C_4H_9(n)$ | $C_4H_9(n)$ | |

TABLE I-continued (R₁ = phenyl with R₁, R₂, R₃ substituents)

| # | | R₂ | R₃ | X | m | n | R₈ | R₉ | R₁₀ | |
|---|---|---|---|---|---|---|---|---|---|---|
| 46 | 4-pyridyl (H) | H | H | Cl | — | 0 | C₆H₅ | C₆H₅ | C₆H₅ | |
| 47 | 2-Cl | H | H | Cl | — | 0 | phenyl | phenyl | phenyl | |
| 48 | 3-CF₃ | H | H | CN | — | 0 | CH₂—C₆H₅ | CH₂—C₆H₅ | CH₂—C₆H₅ | |
| 49 | 2-Cl | H | 6-Cl | H | — | 0 | C₆H₅ | C₆H₅ | C₆H₅ | |
| 50 | 4-OCH₃ | 3-Br | H | H | — | 0 | C₄H₉(n) | C₄H₉(n) | C₄H₉(n) | |
| 51 | 3-Cl | H | H | Cl | — | 0 | C₆H₅ | C₆H₅ | C₆H₅ | |
| 52 | 4-t-C₄H₉ | H | H | CN | — | 0 | CH₂—C₆H₅ | CH₂—C₆H₅ | CH₂—C₆H₅ | |
| 53 | 3-CF₃ | H | H | CN | — | 0 | C₆H₅ | C₆H₅ | C₆H₅ | m.p. 40° |
| 54 | 4-NH—CHO | H | H | CH₃ | — | 0 | C₄H₉(n) | C₄H₉(n) | C₄H₉(n) | |
| 55 | 4-NO₂ | H | H | CH₃ | — | 0 | C₆H₅ | C₆H₅ | C₆H₅ | |
| 56 | 2-OCCH₃ (O=) | 3-Cl | 5-Cl | H | — | 0 | CH₂—C₆H₅ | CH₂—C₆H₅ | CH₂—C₆H₅ | |
| 57 | 2-OCNHCH₃ (O=) | 4-CH₃ | 6-CH₃ | H | — | 0 | C₆H₅ | C₆H₅ | C₆H₅ | |
| 58 | 4-C₃H₇(i) | H | H | H | — | 0 | C₄H₉(n) | C₄H₉(n) | CH₃ | |
| 59 | 3-OCH₃ | 4-OCH₃ | H | H | — | 0 | C₂H₅ | C₂H₅ | C₄H₉(n) | |
| 60 | 3-CH₃ | 5-CH₃ | H | H | — | 0 | C₆H₅ | C₆H₅ | C₆H₅ | |
| 61 | 3-NO₂ | H | H | CH₃ | — | 0 | phenyl | phenyl | phenyl | |
| 62 | 4-NO₂ | H | H | CH₃ | — | 0 | C₄H₉(n) | C₄H₉(n) | CH₃ | |
| 63 | 4-OCH₃ | H | H | CH₃ | — | 0 | C₄H₉(n) | C₄H₉(n) | CH₃ | |

| Compound | R₁ | X | m | n | R₈ | R₉ | R₁₀ | Physical data (°C.) |
|---|---|---|---|---|---|---|---|---|
| 64 | naphthyl | CN | — | 0 | C₄H₉(n) | C₄H₉(n) | C₄H₉(n) | m.p. 74–77° |
| 65 | naphthyl | CN | — | 0 | C₆H₅ | C₆H₅ | C₆H₅ | m.p. 176–179° |
| 66 | NH₂CO | CN | — | 0 | C₄H₉(n) | C₄H₉(n) | C₄H₉(n) | oil |
| 67 | NH₂CO | CN | — | 0 | C₆H₅ | C₆H₅ | C₆H₅ | resin |
| 68 | CH₃NH—C(O)—NH—C(O)— | CN | — | 0 | C₄H₉(n) | C₄H₉(n) | C₄H₉(n) | |
| 69 | C₆H₅—NHCNHC(O)(O)— | CN | — | 0 | C₆H₅ | C₆H₅ | C₆H₅ | |
| 70 | thienyl | CN | — | 0 | CH₂C₆H₅ | CH₂C₆H₅ | CH₂C₆H₅ | |
| 71 | chlorothienyl | Cl | — | 0 | C₄H₉(n) | C₄H₉(n) | CH₃ | |
| 72 | methylthienyl | CH₃ | — | 0 | C₆H₅ | C₆H₅ | C₆H₅ | |
| 73 | benzofuranyl | H | — | 0 | C₄H₉(n) | C₄H₉(n) | C₄H₉(n) | |
| 74 | methylenedioxyphenyl | H | — | 0 | CH₂C₆H₅ | CH₂C₆H₅ | CH₂C₆H₅ | |

TABLE I-continued

| | | $R_1$ | | | | | | |
|---|---|---|---|---|---|---|---|---|
| 75 | 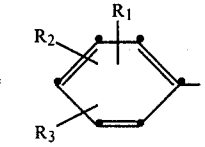 | H | — | 0 | $C_6H_5$ | $C_6H_5$ | $C_6H_5$ | |
| 76 | $COOC_2H_5$ | CN | — | 0 | $C_4H_9(n)$ | $C_4H_9(n)$ | $C_4H_9(n)$ | |
| 77 | 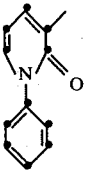 | CN | — | 0 | $C_2H_5$ | $C_2H_5$ | $C_2H_5$ | |
| 78 | $COOC_2H_5$ | $COOC_2H_5$ | — | 0 | $C_6H_5$ | $C_6H_5$ | $C_6H_5$ | |
| 79 |  | O | — | 0 | $C_6H_5$ | $C_6H_5$ | $C_6H_5$ | |
| 80 |  | H | — | 0 | $C_4H_9(n)$ | $C_4H_9(n)$ | $C_4H_9(n)$ | |
| 81 |  | H | — | 0 | $C_4H_9(n)$ | $C_4H_9(n)$ | $CH_3$ | |
| 82 |  | H | — | 0 | $C_6H_5$ | $C_6H_5$ | $C_648 H_5$ | |
| 83 |  | $CH_3$ | — | 0 | $C_4H_9(n)$ | $C_4H_9(n)$ | $C_4H_9(n)$ | |
| 84 |  | H | — | 0 | $CH_2C_6H_5$ | $CH_2C_6H_5$ | $CH_2C_6H_5$ | |
| 85 |  | H | — | 0 | $C_2H_5$ | $C_2H_5$ | $C_4H_9(n)$ | |
| 86 |  | CN | — | 0 | $CH_3$ | $CH_3$ | $CH_3$ | $n_{12}{}^D 1.5195$ |
| 87 |  | $CH_3$ | — | 0 | $C_4H_9(n)$ | $C_4H_9(n)$ | $C_4H_9(n)$ | oil |

Formulation Examples

EXAMPLE 4

Dusts: The following substances are used to formulate (a) 5% and (b) a 2% dust:
(a)
 5 parts of active substance
 95 parts of talc;
(b)
 2 parts of active substance
 1 part of highly dispersed silicic acid
 97 parts of talc.

The active substances are mixed with the carriers and ground and in this form can be processed to dusts for application.

EXAMPLE 5

Granulate: The following substances are used to formulate a 5% granulate:
 5 parts of active substance
 0.25 part of epichlorohydrin
 0.25 part of cetyl polyglycol ether
 3.25 parts of polyethylene glycol
 91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo.

EXAMPLE 6

Wettable powders: The following constituents are used to formulate (a) a 70%, (b) a 40%, (c) and (d) a 25% and (e) a 10% wettable powder:

(a)
- 70 parts of active substance
- 5 parts of sodium dibutylnaphthylsulfonate
- 3 parts of naphthalenesulfonic acid/phenolsulfonic acid/formaldehyde condensate (3:2:1)
- 10 parts of kaolin
- 12 parts of Champagne chalk (b)
- 40 parts of active substance
- 5 parts of sodium ligninsulfonate
- 1 part of sodium dibutylnaphthalenesulfonic acid
- 54 parts of silicic acid (c)
- 25 parts of active substance
- 4.5 parts of calcium ligninsulfate
- 1.9 parts of Champagne chalk/hydroxyethyl cellulose mixture (1:1)
- 1.5 parts of sodium dibutylnaphthalenesulfonate
- 19.5 parts of silicic acid
- 19.5 parts of Champagne chalk
- 28.1 parts of kaolin (d)
- 25 parts of active substance
- 2.5 parts of isooctylphenoxy-polyethylene-ethanol
- 1.7 parts of a Champagne chalk/hydroxyethyl cellulose mixture (1:1)
- 8.3 parts of sodium aluminium silicate
- 16.5 parts of kieselguhr
- 46 parts of kaolin (e)
- 10 parts of active substance
- 3 parts of a mixture of the sodium salts of saturated fatty alcohol sulfates
- 5 parts of naphthalenesulfonic acid/formaldehyde condensate
- 82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for dressing seeds and treating parts of plants.

EXAMPLE 7

Emulsifiable concentrate: The following substances are used to formulate a 25% emulsifiable concentrate:
- 25 parts of active substance
- 2.5 parts of epoxidised vegetable oil
- 10 parts of an alkylarylsulfonate/fatty alcohol polyglycol ether mixture
- 5 parts of dimethyl formamide
- 57.5 parts of xylene.

By diluting such a concentrate with water it is possible to prepare emulsions of the desired concentration, which are especially suitable for treating parts of plants.

Biological Examples

EXAMPLE 8

Pre-emergency antidote test (basic test)

General test method: Small flower pots (diameter 6 cm at the top) are filled with garden soil into which the plant seed is sown, covered with the soil and gently pressed firm. Then the antidote is sprayed as test substance in the form of a dilute solution (obtained from a wettable powder) in an amount corresponding to 4 kg/ha. The herbicide is sprayed onto the soil directly afterwards in corresponding amount. After the pots have stood for 18 days at about 20°–23° C. and 60–70% relative humidity, evaluation is made in accordance with a linear scale from 1 (denoting total damage to the plant) to 9 (denoting undamaged healthy plant). Plants without antidote protection are used as control.

The following herbicides and plants were employed:

(1) 1.5 kg/ha of α-[4-(p-trifluoromethylphenoxy)-phenoxy]-propionic acid n-butoxyethyl ester in maize of the "Orla 264" variety.

(2) 1.5 kg/ha of Metolachlor=N-(-1-methyl-2-methoxyethyl)-N-chloroacetyl-2-ethyl-6-methylaniline in sorghum of the "Funk G-522" variety.

(3) 2 kg/ha of Prometryn=2,4-bis(isopropylamino)-6-methylthio-s-triazine in soybeans.

(4) 2 kg/ha of 4-ethylamino-6-tert-butylamino-2-chloro-s-triazine in wheat of the "Farnese" variety.

(5) 4 kg/ha of Prometryn=2,4-bis(isopropylamino)-6-methylthio-s-triazine in sorghum of the "Funk G-522" variety.

(6) 2 kg/ha of α-[4-(p-trifluoromethylphenoxy)-phenoxy]-propionic acid n-butoxyethyl ester in barley of the "Mazurka" variety.

The following results are obtained with compounds of the formula I:

| Test variant | Compound | Rating of the herbicidal action (with/without antidote) |
|---|---|---|
| 1 | 4 | 3/5 |
| 3 | 4 | 5/7 |
| 3 | 10 | 5/7 |
| 3 | 11 | 5/7 |
| 3 | 12 | 5/7 |
| 1 | 19 | 3/5 |
| 5 | 27 | 1/4 |
| 3 | 28 | 3/5 |
| 5 | 29 | 1/5 |
| 2 | 30 | 2/5 |
| 5 | 38 | 1/3 |
| 3 | 66 | 2/5 |

EXAMPLE 9

Antidote action in transplanted rice on separate application (antidote/pre-emergence, herbicide/post-emergence)

Plastic tubs measuring 8×8×10 cm are filled with wet marshy soil to 2 cm below the edge. A dilute solution of the antidote as test substance is sprayed onto the surface of the soil in an amount corresponding to 4 kg/ha. Rice plants of the "IR-88" variety are transplanted in the 1½- to 2-leaf stage into the prepared tubs. On the next day, the water level is raised to about 1.5 cm. Four days after transplantation, 2-ethylamino-4-(1,2-dimethyl-n-propylamino)-6-methylthio-s-triazine is added to the water in granule form in an amount corresponding to 0.75 kg/ha. During the test, the temperature is 26°–28° C. and the relative humidity 60–80%. Evaluation is made 20 days after the treatment with herbicide, using the same rating as in Example 8. Plants not protected with antidote are used as control. The following results were obtained with compounds of the formula I:

| Compound | Rating of the herbicidal action (with/without antidote) |
|---|---|
| 28 | 4/7 |

EXAMPLE 10

Pre-emergence antidote test in nutrient solution

A Hewitt nutrient solution, which contains the amount of herbicide indicated below as well as 10 ppm of the antidote to be tested, is prepared.

Seeds which would normally be damaged in the indicated test concentrations of the herbicide employed are sown in granular zonolith (expanded vermiculite) in plastic flower pots (diameter 6 cm at the top) which are perforated at the bottom. Each pot is then placed in a second transparent plastic flower pot (diameter 7 cm at the top) which contains about 50 ml of the nutrient solution prepared with herbicide and antidote. This nutrient solution then rises by capillary action in the filling material of the smaller pot and moistens the seed and the germinating plant. The loss in fluid is daily replenished to 50 ml with pure Hewitt nutrient solution. Evaluation is made 3 weeks after the start of the test, using the same rating as in Example 8. The control solution employed in the parallel test contains no antidote.

The herbicides and plants employed are:

(1) 4 ppm of Prometryn=2,4-bis(isopropylamino)-6-methylthio-s-triazine in sorghum of the "Funk G-522" variety.

(2) 4 ppm of 4-ethylamino-6-tert-butylamino-2-chloro-s-triazine in wheat of the "Farnese" variety.

(3) 4 ppm of α-[4-(p-trifluoromethylphenoxy)-phenoxy]-propionic acid n-butoxyethyl ester in barley of the "Mazurka" variety.

(4) 5 ppm of Metolachlor=N-(1-methyl-2-methoxyethyl)-N-chloroacetyl-2-ethyl-6-methaniline in sorghum of the "Funk G-522" variety.

(5) 1 ppm of 2-methoxy-4,6-bis-(5-methoxypropylamino)-s-triazine in sugar beet of the "Kleinwanzleben" variety.

The following results are obtained with compounds of the formula I:

| Test variant | Compound | Rating of the herbicidal action (with/without antidote) |
|---|---|---|
| 1 | 2 | 1/4 |
| 1 | 3 | 1/3 |
| 1 | 6 | 1/3 |
| 1 | 9 | 1/5 |
| 1 | 10 | 1/3 |
| 1 | 15 | 4/6 |
| 1 | 16 | 4/6 |
| 1 | 17 | 1/3 |
| 1 | 18 | 1/3 |
| 1 | 19 | 2/4 |
| 2 | 19 | 4/6 |
| 1 | 27 | 2/4 |
| 2 | 27 | 2/4 |
| 1 | 28 | 2/4 |
| 2 | 28 | 2/5 |
| 1 | 30 | 3/5 |
| 2 | 30 | 5/7 |

-continued

| Test variant | Compound | Rating of the herbicidal action (with/without antidote) |
|---|---|---|
| 1 | 31 | 3/5 |
| 2 | 31 | 5/7 |
| 5 | 36 | 1/5 |

| Test variant | Compound | Rating of the herbicidal action (with/without antidote) |
|---|---|---|
| 1 | 38 | 2/4 |
| 2 | 38 | 3/5 |
| 1 | 53 | 2/4 |
| 2 | 53 | 2/4 |
| 1 | 64 | 1/5 |
| 1 | 65 | 1/5 |
| 1 | 66 | 1/4 |
| 1 | 67 | 1/3 |
| 1 | 87 | 1/4 |

EXAMPLE 11

Post-emergence antidote test in nutrient solution

General test method

Small plastic flower pots (diameter 6 cm at the top), which are perforated at the bottom, are filled with granular zonolith and the seeds are sown in this material. Each pot is then placed in a second transparent plastic flower pot (diameter 7 cm at the top) which contains 50 ml of water which rises by capillary action and moistens the seed. Form the 5th day, the continual loss in water is made up with Hewitt nutrient solution. From the 15th day, when the plant is in the 1½-2-leaf stage, 10 ppm of the antidote to be tested and the amount of herbicide indicated below are added to the nutrient solution which has again been replenished to 50 ml. From the 16th day, the loss in fluid is again made up with pure Hewitt nutrient solution. During the entire duration of the test, the temperature is 20°–23° C. and the relative humidity 60–70%. Evaluation is made 3 weeks after the addition of the herbicide in accordance with the rating employed in Example 8 and subsequent Examples.

Test variants (1) 15 ppm of α-[4-(3,5-dichloropyridyl-2-oxy)-phenoxy]-propionic acid propargylthiolo-ester in wheat of the "Zenith" variety.

(2) 4 ppm of 4-ethylamino-6-tert-butylamino-2-chloro-s-triazine in wheat of the "Zenith" variety.

(3) 2 ppm of α-[4-(p-trifluoromethylphenoxy)-phenoxy]-propionic acid n-butoxyethyl ester in maize of the "Orla" variety.

(4) 8 ppm of α-[4-(p-trifluoromethylphenoxy)-phenoxy]-propionic acid n-butoxyethyl ester in sorghum of the "Funk G-522" variety.

(5) 4 ppm of Prometryn=2,4-bis(isopropylamino)-6-methylthio-s-triazine in sorghum of the "Funk G-522" variety.

(6) 8 ppm of α-[4-(3,5-dichloropyridyl-2-oxy)-phenoxy]-propionic acid methyl ester in wheat of the "Zenith" variety.

A good antidote action is obtained in these test with compounds of the formula (I). The following results are reported by way of example:

| Test variant | Compound | Rating of the herbicidal influence (with/without antidote) |
|---|---|---|
| 2 | 2 | 1/4 |
| 1 | 4 | 4/6 |
| 2 | 6 | 1/4 |
| 5 | 6 | 1/4 |
| 2 | 7 | 1/4 |
| 5 | 7 | 1/5 |
| 2 | 14 | 1/3 |
| 5 | 15 | 1/3 |
| 2 | 17 | 1/4 |
| 5 | 17 | 1/4 |
| 2 | 18 | 1/3 |
| 5 | 18 | 1/5 |
| 5 | 31 | 2/5 |
| 2 | 53 | 1/3 |
| 5 | 53 | 1/5 |
| 2 | 64 | 1/3 |
| 5 | 64 | 1/3 |
| 2 | 65 | 1/4 |
| 5 | 65 | 1/4 |
| 2 | 66 | 1/3 |
| 2 | 67 | 1/4 |
| 5 | 67 | 1/4 |

EXAMPLE 12

Antidote test-seed soaking

Rice seeds of the "IR-8" variety are immersed for 48 hours in solutions of the test substances in concentrations of 10, 100 or 1000 ppm. The seeds are then allowed to dry for about 2 hours until they are no longer tacky. Rectangular plastic tubs (8×8×10 cm) are filled with sandy loam to 2 cm below the edge. 4 g of seeds are sown in each tub and only very loosely covered (to about the diameter of the seed). The soil is kept in a moist (non-marshy) state. Then a dilute solution of the herbicide N-(1-methyl-2-methoxyethyl)-N-chloroacetyl-2-ethyl-6-methylaniline is applied in an amount corresponding to 1.5 kg/ha. Evaluation is made 7 and 18 days after transplantation in accordance with the rating employed in Example 8 and subsequent Examples. A good antidote action is obtained in this test with compounds of the formula (I). The following results are reported by way of example (all at 100 ppm):

| Compound | Rating of the herbicidal action (with/without antidote) |
|---|---|
| 2 | 4/7 |
| 3 | 4/6 |
| 8 | 4/6 |
| 9 | 4/7 |
| 13 | 4/7 |
| 14 | 4/7 |
| 16 | 2/5 |
| 18 | 4/7 |
| 19 | 2/5 |
| 28 | 3/5 |
| 29 | 3/6 |
| 31 | 2/4 |
| 66 | 4/6 |

EXAMPLE 13

Antidote test (root dipping)

Rice plants of the "IR-8" variety are reared in soil until they are in the 1½- to 2-leaf stage and then superficially washed. Then only the roots of the plants, in bunches, are dipped for 45 minutes in a dish containing solutions of the test substance in a concentration of 10, 100 or 1000 ppm. The plants are then transplanted in sandy loam in containers measuring 47×29×24 cm. The surface of the soil is covered with water to a height of 1½ to 2 cm. One day after transplantation, a dilute solution of the herbicide N-n-propoxyethyl-N-chloroacetyl-2,6-diethylaniline is pipetted directly into the water in an amount corresponding to 1.5 kg/ha. Evaluation is made 7 and 18 days after transplantation in accordance with the rating employed in Example 8 and subsequent Examples. Good antidote action is obtained in this test with compounds of the formula (I). The following results are reported by way of example (at 10 ppm):

| Compound | Rating of the herbicidal action (with/without antidote) |
|---|---|
| 5 | 3/6 |
| 8 | 3/5 |
| 67 | 3/6 |

What is claimed is:

1. An oxime derivative of the formula

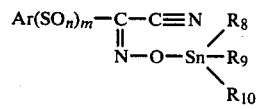

wherein n is 0, 1 or 2, m is 0 or 1,

Ar is alkylphenyl in which the alkyl group has from 1 to 4 carbon atoms, alkoxyphenyl in which the alkyl group has from 1 to 4 carbon atoms, halo-phenyl or naphthyl, and $R_8$, $R_9$ and $R_{10}$ are the same and are $C_1$–$C_4$ alkyl, benzyl or phenyl.

2. An oxime derivative according to claim 1, wherein $R_8$, $R_9$ and $R_{10}$ and are n-butyl or phenyl.

3. A compound selected from the group consisting of

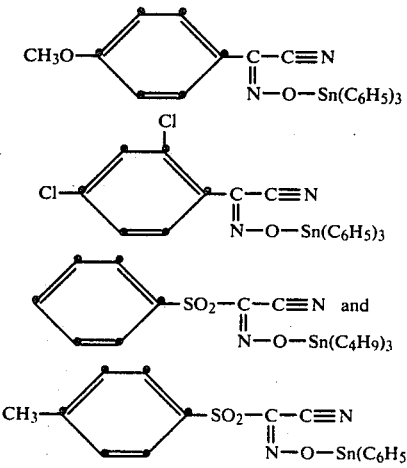

4. A compound selected from the group consisting of

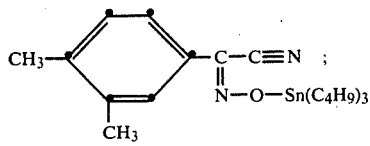
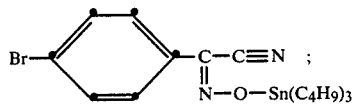
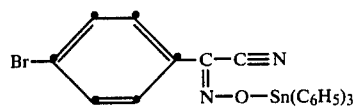
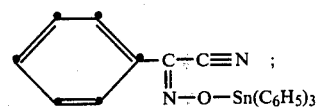
5. The compound according to claim 3 which is
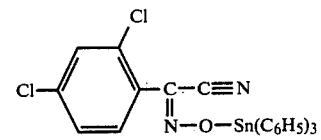
* * * * *